(12) United States Patent
Puffenberger et al.

(10) Patent No.: US 7,632,640 B2
(45) Date of Patent: Dec. 15, 2009

(54) ASSOCIATION OF TSPYL POLYMORPHISMS WITH SIDDT SYNDROME

(75) Inventors: Erik G. Puffenberger, Strafford, PA (US); Dietrich A. Stephan, Phoenix, AZ (US)

(73) Assignee: The Clinic for Special Children, Strasburg, PA (US)

( * ) Notice: Subject to any disclaimer, the term of this patent is extended or adjusted under 35 U.S.C. 154(b) by 294 days.

(21) Appl. No.: 11/007,924

(22) Filed: Dec. 8, 2004

(65) Prior Publication Data

US 2005/0158754 A1 Jul. 21, 2005

Related U.S. Application Data

(60) Provisional application No. 60/527,682, filed on Dec. 8, 2003.

(51) Int. Cl.
C12Q 1/68 (2006.01)
C12P 19/24 (2006.01)
C07H 21/04 (2006.01)

(52) U.S. Cl. ............. 435/6; 536/24.31; 536/24.33
(58) Field of Classification Search ............. 435/6, 435/91.2; 536/24.31, 24.32, 24.33
See application file for complete search history.

(56) References Cited

U.S. PATENT DOCUMENTS 6,642,001 B1 * 11/2003 Bolk et al. ............. 435/6

FOREIGN PATENT DOCUMENTS

WO   WO 01/12659 A2 * 2/2001
WO   WO 0112659 A2 * 2/2001

OTHER PUBLICATIONS

Schnieders, F et al. Testis-specific protein, Y-encoded (TSPY) expression in testicular tissues. Human Molecular Genetics, vol. 5, No. 11, pp. 1801-1807, 1996.*
Database EMBL 'Online'; Jun. 22, 2001; "Sequence 433 from patent WO0140521." XP002326410 retrieved from EBI accesion No. EM_PAT: AX157105 Database accesion No. AX157105; comprises 19 contiguous nucleotides of seq. ID No. 3 including G insertion at 457-458 & WO 01/40521 A (Curagen Corporation Shimkets, Richard, A.; Leach, Martin) Jun. 7, 2001.
Database EMBL 'Online'; Mar. 20, 1996; "yz95a03.s1 Soares melanocyte 2NbHM *Homo sapiens* cDNA clone Image:290764 3' similar to gb∧M87923∧HUMALCE12 Human carcinoma cell-derived Alu RNA transcript, (rRNA); gb:M57627 Interleukin-10 Precursor (Human); mRNA sequence." XP002326411 retrieved from EBI accesion No. EM-EST:N71938. Database accesion No. N71938 comprises 19 contiguous nucleotides of Seq. ID No. 3 including G insertion at 457-458.
Database EMBL 'Online'; Oct. 28, 1997; "nq47g07.s1NCI_CGAP_Co10 *Homo sapiens* cDNA clone Image:1147068 3' similar to gb:L07077 Enoyl-CoA Hydratase (Human); mRNA sequence."; XP002326413 retrieved from EBI accesion No. EM_EST:AA627434. Database accesion No. AA627434 comprises 19 contiguous nucleotides of Seq. ID No. 3 including G insertion at 457-458.
Database EMBL 'Online'; Jun. 22, 2001; "Sequence 1716 from Patent WO140521." XP002326414 retrieved from EBI accesion No. EM_PAT: AX158388 comprises Database accesion No. AX158388 comprises 19 contiguous nucleotides of Seq. ID No. 3 including G insertion at 457-458 & WO 01/40521 A (CUragen Corporation Shimkets, Richard A; Leach, Martin) Jun. 7, 2001.
Database EMBL 'Online! Jun. 22, 2001; "Sequence 2540 from Patent WO0140521"; XP002326414 retrieved from EBI accesion No. EM_PAT:AX159212 Database accesion No. AX159212 comprises 19 contiguous nucleotides of Seq. ID No. 3 including G insertion at 457-458 & WO 01/40521 A (Curagen Corporation; Shimkets, Richard, A; Leach, Martin).
Database DBSNP 'Online! NCBI; Jan. 8, 2002; XP002326647 retrieved from NCBI accesion No. REF SNP ID: RS3749894 Database accesion No. RS3749894 HTTP://www.NCI.NLM.NIH.GOV/SNP/SNP_REF.CGI?RS=3749894 abstract.
Database EMBL 'Online! Mar. 20, 2003, "*Homo sapiens* TSPY-like 1, mRNA (cDNA clone MGC:57205 Image: 5297724), complete cds." XP002326412 retrieved from EBI accesion No. EM_HUM:BC048969 Database accesion No. BC048969 abstract.
Vogel et al; "Murine and human TSPY-SEt-nap1L1 family" Cytogenetics and Cell Genetics, Basel, Ch, vol. 81, No. 3-4, 1998, pp. 265-270, XP002952970.
Opdal Siri H. et al, "possible role of mtDNA mutations in sudden infant death", Pediatric Neurology, Jul. 2002, vol. 27, No. 1, Jul. 2002, pp. 23-29, XP002326646.
Puffenberger Erik G, et al., "Mapping of sudden infant death with dysgenesis of the testes syndrome (SIDDT) by a SNP genome scan and identification of TSPYL loss of function", Proceedings of the National Academy of Sciences of the United States of America; Aug. 10, 2004, vol. 101, No. 32., pp. 11689-11694.

* cited by examiner

*Primary Examiner*—Suryaprabha Chunduru
(74) *Attorney, Agent, or Firm*—Sandra E. Wells

(57) ABSTRACT

The identification of a novel mutation in the testis specific Y-like gene and association of the mutation with SIDDT syndrome are disclosed. Methods for diagnosing SIDDT syndrome are disclosed. Methods for identifying compounds for use in the diagnosis and treatment of disorders associated with mutation in the TSPYL gene are also disclosed. The invention therefore provides nucleic acid sequences, genes, polypeptides, antibodies, vectors containing the gene, host cells transformed with vectors containing the gene, animal models for the disease, methods for expressing the polypeptide, genetic screening methods and kits, diagnostic methods and kits.

9 Claims, 6 Drawing Sheets

Figure 1A. TSPYL wild type

```
  1 msgldgvkrt tplqthsiii sdqvpsdqda hqylrlrdqs
    eatqvmaepg eggsetvalp ppppseeggv pqdaagrggt
    pqirvvggrg hvaikagqee gqppaeglaa asvvmaadrs
121 lkkgvqggek aleicgaqrs aseltagaea ea*eevktgkc
    atvsaavaer esaevvkegl aekevmeeqm eveeqppege
    eievaeedrl eeeareeegp wplhealrmd pleaiqleld
241 tvnaqadraf qqlehkfgrm rrhylerrny iiqnipgfwm
    tafrnhpqls amirgqdaem lryitnlevk elrhprtgck
    fkfffrrnpy frnklivkey evrssgrvvs lstpiiwrrg
361 hepqsfirrn qdlicsfftw fsdhslpesd kiaeiikedl
    wpnplqyyll regvrrarrr plrepveipr pfgfqsg
    (SEQ ID NO: 1)
*indicates position of insertion
```

Figure 1B. TSPYL 457_458insG

```
  1 msgldgvkrt tplqthsiii sdqvpsdqda hqylrlrdqs
    eatqvmaepg eggsetvalp ppppseeggv pqdaagrggt
    pqirvvggrg hvaikagqee gqppaeglaa asvvmaadrs
121 lkkgvqggek aleicgaqrs aseltagaea eagggedrkv rhrlssrg
    (SEQ ID NO: 2)
```

Figure 2A TSPYL wild type mRNA

```
   1 agtgagactg tagggtgggc ggtgcgagcg gcggttagct cccagttcgg cctctgagga
  61 aaacgggcgt tcgcctgcgg ttggtccgac tgttagcaac AUGagcggcc tggatggggt
 121 caagaggacc actcccctcc aaacccacag catcattatt tctgaccaag tcccgagcga
 181 ccaggacgca caccagtacc tgaggctccg cgaccaaagc gaggcgacac aggtgatggc
 241 ggagccgggt gagggaggct cggagaccgt cgcgctcccg cctccaccgc cttcagagga
 301 gggggggcgta ccccaggatg ccgcgggccg tggcggtact ccccagatcc gagttgttgg
 361 gggtcgcggt catgtggcga tcaaagccgg gcaggaagag ggccagcctc ccgccgaagg
 421 cctggcagcc gcttctgtgg tgatggcagc cgaccgcagc ctgaaaaagg gcgttcaggg
 481 tggagagaag gccctagaaa tctgtggcgc ccagagatcc gcgtctgagc tgacggcggg
 541 ggcggaggct gaggcggagg aggtgaagac aggaaagtgc gccaccgtct cagcagccgt
 601 ggctgagagg gagagcgctg aggtggtggt gaaggaaggc ctggcggaga aggaggtaat
 661 ggaggagcag atggaggtag aggagcagcc gccagaaggt gaagaaatag aagtggcgga
 721 ggaggataga ttggaggagg aggcgaggga ggaagaaggg ccctggcctt tgcatgaggc
 781 tctccgcatg gaccctctgg aggccatcca gctggaactg gacactgtga atgctcaggc
 841 cgacagggcc ttccaacagc tggagcacaa gtttgggcgg atgcgtcgac actacctgga
 901 gcggaggaac tacatcattc agaatatccc gggcttctgg atgactgctt ttcgaaacca
 961 cccccagttg tccgccatga ttaggggcca agatgcagag atgttaaggt acataaccaa
1021 tttagaggtg aaggaactca gacaccctag aaccggttgc aagttcaagt tcttctttag
1081 aagaaacccc tacttcagaa acaagctgat tgtcaaggaa tatgaggtaa gatcctccgg
1141 ccgagtggtg tctctttcta ctccaattat atggcgcagg gggcatgaac cccagtcctt
1201 cattcgcaga aaccaagacc tcatctgcag cttcttcact tggttttcag accacagcct
1261 tccagagtcc gacaaaattg ctgagattat taaagaggat ctgtggccaa atccactgca
1321 atactacctg ttgcgtgaag gagtccgtag agcccgacgt cgccgctaa gggagcctgt
1381 agagatcccc aggcccttt g ggttccagtc tggtTAAcat ttgcccttgg gaatactcct
1441 gcacaaggtc tcctaccacc ttctgctgga cctgtgcttg ggcatcagca atgagtatgc
1501 cttctattgt gctttgtttt tgctgacttt tatgcaccct gtttcctttg gatattcagt
1561 tctctcaacc tcaagattga gacggtggtg ggtatgcttc tccacttcca tatgaccttc
1621 atgctgttct ggaatatcac atgctacgag gtcatcccttc acactacttg taagccaagc
1681 aaatgatact gtagattgta ctgcctttat ctgcactgct ggaccctgt ttattcccag
1741 ggcctctgaa ctggttgctg tcacttggat ttctagcttt gggagcctgt tccacctact
1801 cagctctgca ttgagcagta tgggcacatg ccctgtggac agttactgga cgttaatgaa
1861 ctcagaggag aaaagcagtg agccacttgt tctgtgtgat ttatggtact tcattgctct
1921 tccttcacct ctagtcactt tctattgcta cctgccctac attggctcct gccaaggtcc
1981 ctctctctcc ctgttttcct ttttttttt ttttttttt tgagacggag acggagtct
2041 tgctctgtcg cccaggttgg agtgcagtgg cgcgatctcg gctcactgca acctccacct
2101 cccgggttca agcgattctc ctgcctcagc ctcccgagta gctgggacta caggcgcgcg
2161 ccgccacgcc cggctaattt ttatatttt agtagagacg gggtttcacc atgctggcca
2221 ggctggtctc gaaccccgac ctcgtgatcc gccctcctta gcctcccaat cctctcttaa
2281 aaaagtgata gctcagaaac atttgtaaaa gcaaggtttt tatttcattt tggctctgtc
2341 attttcagag gcaaagaagt tggcctgtaa aatagagtgc tagagctctt acgcccctcc
2401 ccttcttccc aacttcctac ttcctagccc ttttatcaac tcctagaata gttaaagaga
2461 gacacatcta gatgggatga aaggtgccct aagcaggaga aactgaacaa aaggctagag
2521 gcatgggcca ggtaaaaatt gggcctagag tgaagactgt gctgtcgtta agagctttcg
2581 aggaaggagt acttactccc caatgatgat gaatggaaaa atacttttca gggagaattg
2641 aaggggttaa agtgttaaat atgttgccta gacaagggtt ctttaaagaa agacagcgca
2701 actttgaatg ctttcttact tgttttgtga cctaatttat gtggaagatt gttatttcat
2761 taggatttag taaaatttt ttttctgatt ctaaacttat tgtgaaaatt gagctgtaca
2821 gatattcttt tgatttcaat tgggaacatt tggaagaaca acagtcttac ttgcctgtac
2881 aatatagaga catatgaata gtcataacag ttttcaactt gttcttgttt ctgttaaact
2941 atattcctag aaacatagtt tgaacaactt ggtctttgtt aggcttgtca aattgcttc
3001 atggaaaaat aatctacaaa agtatggttt aattgattgt cttacatgat aattttccct
3061 ggtaacaact tagtaagtga tatatctttt ttcctaaatt gcttaaatac tgtgaaattg
3121 ctctgacaaa ttggaagtgt accattggca tatttgtctt ccttttatg catgatggta
3181 aaataaaagc atgttgttct gctaaaaaaa aaaaaaaaa aaaaaaaaa aaaaaaaaa
3241 aacaaaaaaa aaaaaaaa (SEQ ID NO:3)
```

Figure 2B TSPYL 457_458insG mRNA

```
1     agtgagactg tagggtgggc ggtgcgagcg gcggttagct cccagttcgg
      cctctgagga aaacgggcgt tcgcctgcgg ttggtccgac tgttagcaac
      AUGagcggcc tggatggggt caagaggacc actcccctcc aaacccacag
      catcattatt tctgaccaag tcccgagcga ccaggacgca caccagtacc
      tgaggctccg cgaccaaagc gaggcgacac aggtgatggc ggagccgggt
      gagggaggct cggagaccgt cgcgctcccg cctccaccgc cttcagagga
301   gggggcgta ccccaggatg ccgcgggccg tggcggtact ccccagatcc
      gagttgttgg gggtcgcggt catgtggcga tcaaagccgg caggaagag
      ggccagcctc ccgccgaagg cctggcagcc gcttctgtgg tgatggcagc
      cgaccgcagc ctgaaaaagg gcgttcaggg tggagagaag gccctagaaa
      tctgtggcgc cagagatcc gcgtctgagc tgacggcggg ggcggaggct
      gaggcggGagg aggtgaagac aggaaagtgc gccaccgtct cagcagccgt
602   ggcTGAgagg gagagcgctg aggtggtggt gaaggaaggc ctggcggaga
      aggaggtaat ggaggagcag atggaggtag aggagcagcc gccagaaggt
      gaagaaatag aagtggcgga ggaggataga ttggaggagg aggcgaggga
      ggaagaaggg ccctggcctt tgcatgaggc tctccgcatg accctctgg
      aggccatcca gctggaactg gacactgtga atgctcaggc cgacagggcc
      ttccaacagc tggagcacaa gtttgggcgg atgcgtcgac actacctgga
902   gcggaggaac tacatcattc agaatatccc gggcttctgg atgactgctt
      ttcgaaacca cccccagttg tccgccatga ttaggggcca agatgcagag
      atgttaaggt acataaccaa tttagaggtg aaggaactca gacaccctag
      aaccggttgc aagttcaagt tcttctttag aagaaccccc tacttcagaa
      acaagctgat tgtcaaggaa tatgaggtaa gatcctccgg ccgagtggtg
      tctctttcta ctccaattat atggcgcagg gggcatgaac cccagtcctt
1202  cattcgcaga aaccaagacc tcatctgcag cttcttcact tggttttcag
      accacagcct tccagagtcc gacaaaattg ctgagattat taaagaggat
      ctgtggccaa atccactgca atactacctg ttgcgtgaag gagtccgtag
      agcccgacgt cgcccgctaa gggagcctgt agagatcccc aggcccttttg
      ggttccagtc tggttaacat ttgcccttgg gaatactcct gcacaaggtc
      tcctaccacc ttctgctgga cctgtgcttg ggcatcagca atgagtatgc
1502  cttctattgt gctttgtttt tgctgacttt tatgcaccct gtttcctttg
```

Figure 2B continued

```
        gatattcagt tctctcaacc tcaagattga gacggtggtg ggtatgcttc
        tccacttcca tatgaccttc atgctgttct ggaatatcac atgctacgag
        gtcatccttc acactacttg taagccaagc aaatgatact gtagattgta
        ctgcctttat ctgcactgct tggaccctgt ttattcccag ggcctctgaa
        ctggttgctg tcacttggat ttctagcttt gggagcctgt tccacctact
  1802 cagctctgca ttgagcagta tgggcacatg ccctgtggac agttactgga
        cgttaatgaa ctcagaggag aaaagcagtg agccacttgt tctgtgtgat
        ttatggtact tcattgctct tccttcacct ctagtcactt tctattgcta
        cctgccctac attggctcct gccaaggtcc ctctctctcc ctgttttcct
        tttttttttt tttttttttt tgagacggag gacggagtct tgctctgtcg
        cccaggttgg agtgcagtgg cgcgatctcg gctcactgca acctccacct
  2102 cccgggttca agcgattctc ctgcctcagc ctcccgagta gctgggacta
        caggcgcgcg ccgccacgcc cggctaattt ttatattttt agtagagacg
        gggtttcacc atgctggcca ggctggtctc gaaccccgac ctcgtgatcc
        gccctcctta gcctcccaat cctctcttaa aaagtgata gctcagaaac
        atttgtaaaa gcaaggtttt tatttcattt tggctctgtc attttcagag
        gcaaagaagt tggcctgtaa aatagagtgc tagagctctt acgcccctcc
  2402 ccttcttccc aacttcctac ttcctagccc ttttatcaac tcctagaata
        gttaaagaga gacacatcta gatgggatga aaggtgccct aagcaggaga
        aactgaacaa aaggctagag gcatgggcca ggtaaaaatt gggcctagag
        tgaagactgt gctgtcgtta agagctttcg aggaaggagt acttactccc
        caatgatgat gaatggaaaa atacttttca gggagaattg aaggggttaa
        agtgttaaat atgttgccta gacaagggtt ctttaaagaa agacagcgca
        actttgaatg cttctttact tgttttgtga cctaatttat gtggaagatt
        gttatttcat taggatttag taaaattttt ttttctgatt ctaaacttat
        tgtgaaaatt gagctgtaca gatattcttt tgatttcaat tgggaacatt
        tggaagaaca acagtcttac ttgcctgtac aatatagaga catatgaata
        gtcataacag ttttcaactt gttcttgttt ctgttaaact atattcctag
        aaacatagtt tgaacaactt ggtctttgtt aggcttgtca aattgccttc
  3002 atggaaaaat aatctacaaa agtatggttt aattgattgt cttacatgat
        aattttccct ggtaacaact tagtaagtga tatatctttt ttcctaaatt
        gcttaaatac tgtgaaattg ctctgacaaa ttggaagtgt accattggca
        tatttgtctt ccttttatg catgatggta aaataaaagc atgttgttct
```

Figure 2B continued

```
gctaaaaaaa aaaaaaaaaa aaaaaaaaaa aaaaaaaaaa aacaaaaaaa
aaaaaaaaa (SEQ ID NO:4)
```

Figure 3.

```
5' gcgtctgagc tgacggcggg ggcggaggct gaggcggGagg aggtgaagac aggaaagtgc gccaccgtct -3' (SEQ ID NO: 5)
```

ASSOCIATION OF TSPYL POLYMORPHISMS WITH SIDDT SYNDROME

RELATED APPLICATIONS

This application claims the benefit of U.S. Provisional Application No. 60/527,682, filed Dec. 8, 2003. The entire teachings of the above application are incorporated herein by reference.

GOVERNMENT SUPPORT

This invention was made with government support under federal grant no. 1U24NS04357-01 awarded by the National Institute of Neurological Disorders and Stroke. The United States Government may have certain rights in this invention.

SEQUENCE LISTING

The sequence listing provided herein is hereby incorporated by reference in its entirety.

BACKGROUND OF THE INVENTION

SIDDT syndrome is a previously undescribed disease that presents with a variety of clinical symptoms including respiratory arrest leading to death by six months of age, ambiguous genitalia, and cranial nerve palsy. The disorder has only been seen in the Old Order Amish population, and is inherited in an autosomal recessive fashion. Historically the syndrome has been unexplained, no diagnostic tests were available, and clinical recognition in the neonate was difficult, particularly in affected females.

SUMMARY OF THE INVENTION

A method of identifying individuals who are carriers of a mutation associated with SIDDT syndrome and individuals who are likely to be affected by SIDDT syndrome are disclosed. An association between a mutation in the Testis Specific-Protein Y-Like gene (TSPYL) and SIDDT syndrome is described. Sequence analysis of the gene in samples from affected individuals revealed the presence of a nonsense mutation at amino acid 169 of the protein resulting from an insertion of a guanine at position 457 of the coding region, 457_458insG.

In one embodiment an isolated nucleic acid molecule is disclosed. The isolated nucleic acid molecule comprises a sequence selected from the group consisting of: a nucleotide sequence that encodes a polypeptide comprising the amino acid sequence of SEQ ID NO: 2 or the complement of said nucleotide sequence; a nucleotide sequence comprising SEQ ID NO: 4 or its complement; and, an oligonucleotide comprising at least 16 contiguous nucleotides of SEQ ID NO: 3 or its complement, wherein the oligonucleotide includes an insertion of a nucleotide at position 457_458. The mutation identified has an insertion of a guanine at this position, 457_458insG, but in other embodiments the insertion may be another base, for example, adenine, cytosine or thymine. Any single base insertion at this position, or at another position in the coding region upstream of amino acid 169, would result in the in frame stop codon at amino acid position 169, resulting in a truncated protein. Any mutation in the coding region that would result in a non-functional protein or a mutation in a regulatory region that alters the expression of the gene, for example, by altering transcription levels, mRNA stability or mRNA processing may also have a disease phenotype. Other mutations that result in truncation of the protein are also likely to result in a disease phenotype.

In many embodiments methods of detecting a mutant TSPYL gene or gene product are disclosed. The mutation may be detected, for example, by hybridizing an isolated nucleic acid sequence described above to a nucleic acid sample and detecting hybridization. The isolated nucleic acid sequence may be labeled or the nucleic acids in the nucleic acid sample may be labeled. One or more of the nucleic acids may be attached to a solid support such as an array, a membrane or a bead.

The methods may be used to determine if a subject carries a mutant TSPYL gene associated with SIDDT syndrome by detecting a TSPYL 457_458insG gene or gene product in a biological sample from the subject. The step of determining may comprise performing an in vitro nucleic acid assay, for example PCR. The PCR may be with allele specific probes so that amplification is present if the allele is present and absent if the allele is absent. Hybridization with allele specific probes may also be used to detect the mutant allele.

In one embodiment a nucleic acid probe spanning the 457_458insG mutation in the TSPYL gene is hybridized to a nucleic acid sample from an individual and if hybridization is detected this is an indication that the 457_458insG mutation is present. The probe may be directed to either strand of the double stranded DNA or to the mRNA. The absence of the mutation could also be detected, for example, by a probe that hybridizes to the 457_458 region only in the absence of the mutation, i.e. only hybridizes to the wild type. Since the deleterious effect of the mutation seems to result from the introduction of a downstream stop condon, any single base insertion at that position would be expected to have the same phenotype. Therefore, the mutation to be detected in one aspect is 457_458insN where N can be A, G, C, T or U. In one aspect the probe may have a degenerate base at the position corresponding to the insertion so that it will hybridized specifically to all possible single base insertions at the insertion position.

In another embodiment the presence or absence of a mutant TSPYL polypeptide is detected. The TSPYL polypeptide may be detected, for example, using an antibody to a TSPYL polypeptide. The antibody may be capable of distinguishing between the mutant (SEQ ID NO: 2) and wild type (SEQ ID NO: 1) proteins or the antibody may be directed to an epitope present in both the mutant and wild type proteins. Differences in size, for example, may be used to distinguish the mutant and wild type proteins, for example, by differences in mobility on a gel.

Screening for the mutation may be performed on an individual to determine if the individual is a carrier. Individuals who are heterozygous for the 457_458insG mutation are carriers. Testing may also be performed in utero to determine if the offspring of a known or suspected carrier will be affected with SIDDT syndrome. Testing may be done on a human conceptus or fetus and may be done in utero or in vitro. Neonates may also be tested to determine if the mutation is present and if it is present if the individual is homozygous or heterozygous.

In some embodiments kits that may be used for assaying for the presence of a mutant TSPYL gene are disclosed. Components of the kit may include one or more oligonucleotide probes which specifically bind to a mutant TSPYL gene; and one or more reagents that may be used for detecting the hybridization of the oligonucleotide probe to the mutant, for example, the TSPYL 457_458insG gene or gene product; wherein the probe and reagents are present in amounts effective to perform the hybridization assay. In another embodiment a kit for assaying for the presence of a 457_458insN mutation in a TSPYL gene is disclosed. The kit may contain primers for allele specific PCR amplification or allele specific hybridization. In one embodiment the kit comprises a first primer that is specific for the 457_458insN mutation, a second primer that is specific for the wild type allele and a third primer that hybridizes to both alleles in a region outside of the 457_458insN region. The primers may be used in separate PCR reactions so that if the mutant allele is present, an amplification product is generated in a reaction with the first and third primers and if the wild type allele is present an amplification product is generated in a reaction with the second and third primers. The kits may also contain one or more thermally stable polymerases, dNTPs and mixtures thereof, one or more buffers and instructions for use of the kit for genotyping the TSPYL gene.

Any method known in the art for mutation detection may be used to detect a TSPYL mutation associated with SIDDT or another disease. Methods that may be used include, for example, single base extension, oligonucleotide ligation assay, molecular inversion probe assays, allele specific primer extension with sequence coded identity tags and allele specific hybridization.

In another embodiment an antibody to a wild type or mutant TSPYL protein is disclosed. In one aspect of the invention, an antibody that binds to the mutant TSPYL protein and not the wild type TSPYL protein is disclosed.

BRIEF DESCRIPTION OF THE FIGURES

FIG. 1A shows the wild type protein. An asterisk marks the location of the insertion in the mutant protein.

FIG. 1B shows the truncated mutant protein resulting from the 457_458insG mutation.

FIG. 2A shows a wild type mRNA sequence for TSPYL. The coding region is underlined and the initiator AUG and stop codon are shown in bold.

FIG. 2B shows a mutant mRNA sequence for TSPYL carrying the 457_458insG mutation. The initiator AUG, the inserted G and the now in-frame stop codon at position 169 of the protein are shown in bold and underlined.

FIG. 3 shows the 457_458insG mutation including 70 additional bases of upstream and downstream flanking sequence.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, fungi, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual*, E. Harlow et al. (1998), *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

For a discussion of genotyping analysis methods see, for example, Elena and Lenski *Nat. Rev. Genet.* 4:457-469 (2003), Twyman and Primrose, *Pharmacogenomics* 4:67-79 (2003), Hirschhorn et al., *Genetics in Medicine* 4:45-61 (2002) and Glazier et al., *Science* 298:2345-2349 (2002). For a discussion of high throughput genotyping approaches see, for example, Jenkins and Gibson, *Comp. Func.t Genom.*, 3:57-66 (2002). For a review of methods of haplotype analysis in population genetics and association studies see, for example, Zhao et al. *Pharmacogenomics* 4:171-178 (2003).

B. Definitions

In order to facilitate review of the various embodiments of the invention and an understanding of various elements and constituents used in making the invention and using same, the following definition of terms used in the invention description is as follows:

A SIDDT syndrome carrier is an individual in apparent health whose chromosomes contain a mutant TSPYL1 gene that may be transmitted to that person's offspring. A SIDDT syndrome patient is an individual who is homozygous for the 457_458insG mutation in the TSPYL gene.

A genome is all the genetic material of an organism. In some instances, the term genome may refer to the chromosomal DNA. Genome may be multichromosomal such that the DNA is cellularly distributed among a plurality of individual chromosomes. For example, in a human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a cell which is derived from chromatin and which comprises DNA and protein components (especially histones). The conventional internationally recognized individual human genome chromosome numbering system is employed herein. The size of an individual chromosome can vary from one type to another within a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at a frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form or allele and other allelic forms are designated as alternative or variant alleles. The allelic form occurring most frequently in a selected population is sometimes referred to as the wild type form. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Single nucleotide polymorphisms (SNPs) are positions at which two alternative bases occur at appreciable frequency (>1%) in a given population. SNPs are the most common type of human genetic variation. A polymorphic site is frequently preceded by and followed by highly conserved sequences (e.g., sequences that vary in less than $\frac{1}{100}$ or $\frac{1}{1000}$ members of the populations).

A SNP may arise due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the A allele, and those individuals who have one copy of each allele are heterozygous. An array can be designed to distinguish between each of these three possible outcomes. A polymorphic location may have two or more possible alleles and the array may be designed to distinguish between all possible combinations.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur at equal frequency, and linked locus Y has alleles c and d, which occur at equal frequency, one would expect the combination ac to occur at a frequency of 0.25. If ac occurs more frequently, then alleles a and c are in linkage disequilibrium. Linkage disequilibrium may result, for example, because the regions are physically close, from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

LOD scores are calculated by estimating a linkage distance of specific genes or markers, and, given that estimate, calculating the probability of a given birth sequence. That value is divided by the probability of a birth sequence if the genes or markers (SNPs) are unlinked. The log of this value is calculated by iterating this process over several estimated linkage distances. The highest LOD score is determined and this is the score that likely represents the best estimate for linkage distance give the pedigree and the SNP of interest. LOD score=log(probability of birth with a given linkage value/P of birth with no linkage).

Sudden Infant Death Syndrome (SIDS) is defined as the sudden death of an infant under one year of age which remains unexplained after a thorough case investigation, including performance of a complete autopsy, examination of the death scene, and review of the clinical history. For a discussion of gene polymorphisms that may predispose infants to SIDS see Opdal and Rognum, *Pediatrics* 114(4): e506 (2004). It is unlikely that there is a single mutation that is the predisposing factor in all SIDS cases, but it is likely that there are one or more genes that when mutated predispose infants to sudden infant death, possibly in combination with environmental factors, for example, prone sleeping position, overheating, and infection or illness.

Identification of Genetic Lesion Associated with Sudden Infant Death with Dysgenesis of the Testes Syndrome (SIDDT)

SIDDT (Online Mendelian Inheritance in Man (OMIM) accession no. 608800) is a recently discovered disorder found in the Belleville Amish Community. Clinical recognition of the syndrome has historically been difficult, particularly in affected females. Infants with SIDDT syndrome appear normal at birth, develop signs of visceroautonomic dysfunction early in life, and die before 12 months of age of abrupt cardiorespiratory arrest. Caretakers of affected infants say that at birth the infants often have an unusual cry, which is a staccato sound, similar to the cry of a goat.

Affected newborns appear to be normal but are difficult to feed and usually require nasogastric tube alimentation. Signs of abnormal autonomic and visceral nerve regulation manifest within the first months of life and include neonatal bradycardia, hypothermia, severe gastoresophageal reflux, laryngospasm, bronchospasm, and abnormal cardiorespiratory patterns during sleep. The infants typically have a pathological startle reflex that includes obstructive apnea and appears similar to breath-holding. The startle can be provoked by loud noise, bright light, movement or tactile stimulation and is unresponsive to clonazepam. Although seizure like movements have been described by parents, EEGs were normal for several cases. Bulbar and cervical anterior horn cell dysfunction or degeneration may be part of the neurological basis for abnormal airway control and dysphagia.

Neuropathological exams of two infants showed that brain and peripheral nerves were normal, there was no dysplasia or inflammation of the brainstem and no pathology of cervical anterior horn cells or lower motor neurons of the hypoglossal nerve. Affected individuals do have signs of progressive craniocervical and upper thoracic motor unit dysfunction, for example, signs of cranial nerve palsy including tongue fasciculation, ocular palsies, symmetric weakness of the facial nerve, and decreased reflexes in the upper extremities.

Males with SIDDT syndrome have fetal testicular dysgenesis and ambiguous genitalia and can be mistaken for females. The basis of the ambiguous genitalia is fetal testicular dysgenesis; however, there is normal regression of Mullerian structures. Therefore, Sertoli cells secrete Mullerian inhibiting hormone, but the Leydig cells do not sustain production of testosterone and dihydrotestosterone throughout fetal life. The development of male genitalia arrests at variable embryologic stages. At birth some males may be identified as females on the basis of external genitalia, but other male infants have demonstrated fusion and rugation of the gonadal sack and some development of the penile shaft. Such variable maturation of male genitalia indicates early fetal exposure to testosterone and suggests that testicular failure occurs at different times in fetal development. Female development is normal including all external and internal genitalia and reproductive endocrine functions. Despite the differences in sexual differentiation, females and males have the same severity of neurological dysfunction and die at the same age, with autopsy reports being uninformative.

A collection of samples from individuals affected with SIDDT syndrome, their parents, siblings and extended family members were genotyped using the Affymetrix Mapping 10K Array Xba 131. For genotyping methods using the Mapping 10K array see, Kennedy et. al. *Nat. Biotech.* 21:1233-1237, (2003). The SIDDT syndrome pedigree is comprised of four affected individuals and their parents from three sibships. For a diagram of SIDDT in a consanguineous Old Order Amish pedigree see FIG. 1 of Puffenberger et al. *PNAS* 101:11689-11694 (2004), which is incorporated herein by reference in its entirety for all purposes. The genome-wide linkage scan conducted on the multiplex SIDDT pedigree rapidly and unambiguously mapped the disorder to 6q22 with a location score of 8.11 [maximum 2-point logarithm of odds (LOD) of 2.41], in a 3.6 Mb interval. Sequencing of two candidate genes in the region identified a nonsense mutation in the testis-specific Y-like gene (TSPYL). The region that received the highest 2-point LOD score (4.7) was on chromosome 6q22.1c-q22.2d and extended from bases 113744706 to 115890416 (Build 34 of the NCBI human genome sequence). The individual genotypes for 13 homozygous SNPs in affected individuals are shown in Table 1. The homozygous segment spanned 3.6 Mb corresponding to roughly 1.1 cM.

Genetic and physical map of the SIDDT syndrome locus including the TSPYL gene may be found in Puffenberger et al. *PNAS* 101:11689-11694 (2004), which is incorporated herein by reference in its entirely for all purposes. The SNP autozygous haplotype was comprised of 13 homozygous SNPs bounded by rs 1388219 and rs 1321370 across 1.1 Mb. Thirty seven known and hypothetical genes reside within the interval, including TSPYL and TSPYL4. TSPYL4 showed no coding region SNPs upon sequencing the gene in affected individuals.

The SIDDT phenotype included testicular dysgenesis, so TSPYL was analyzed because it has a sequence similarity of 38-40% homology compared to the Y-linked testis-specific protein (TSPY), which maps to chromosome Yp11. This homology indicates that TSPYL may have a function related to sexual differentiation and testicular development. TSPYL is broadly expressed in the testis, ovaries, prostates, brain, spleen kidney, lung, heart and liver and contains a domain common to nucleosome assembly proteins (NAPs) and a domain that has homology to DNA binding domains. The coding sequence of the TSPYL gene is 1314 bases in length (Genbank accession number BC048969 which is incorporated herein in its entirety by reference) and lacks introns (Genbank accession number AL050331 which is incorporated herein in its entirety by reference). The TSPYL protein is a 437 amino acid protein, FIG. 1A (SEQ ID NO: 1). The GenBank accession number for the protein is XP_371844. FIG. 1B shows the mutant protein resulting from the 457_458insG mutation. An mRNA with the wild type sequence is shown in FIG. 2A, SEQ ID NO: 3.

As described herein, complete sequencing of the TSPYL gene revealed a homozygous single base insertion at position 457 of the coding region in affected individuals, FIG. 2B, SEQ ID NO: 4. The 457_458insG causes a missense mutation at amino acid 153 and results in premature truncation of the protein at amino acid 169. The sequence of the truncated protein is shown in FIG. 1B, SEQ ID NO: 2. This change was not seen as a polymorphic variant in the SNP database or in GenBank. Truncation of the TSPYL protein at amino acid 169 results in inappropriate subcellular targeting of TSPYL and loss of the NAP domain, suggesting that the protein is non-functional. Loss of the NAP functional domain may affect the ability of the protein to shuttle histones from the cytoplasm to the nuclease and disrupts the nuclear localization signal on the tertiary surface of the peptide. Example 3 below demonstrated that the truncated mutant protein, lacking the NAP domain, has altered subcellular localization compared to the wild type protein. The mutant shows diffuse cytoplasmic staining in contrast to the wild type which shows punctate staining and localization to the nucleus. This protein is predicted to be involved in the male sexual differentiation pathway, and the truncation may result in aberrant male sexual differentiation, neurological dysfunction, and fatal sleep apnea. For additional discussion of male sexual differentiation see, Olaf Hiort and Paul-Martin Holterhus, *Eur J. Endo.* 142: 101-110, (2000).

In addition to the 457_458insG mutation, two polymorphic variants were detected while sequencing control samples: a known nonsynonymous SNP 541G/A (A181T, rs3749894) and a unique in-frame short tandem repeat [523 $(GTG)_{2-3}$] that codes for either two or three adjacent valine residues at positions 175-177 in the peptide. The 541A allele had a frequency of 7.8% whereas the 523$(GTG)_2$ allele had a frequency of 30.2% on control chromosomes. The position of the two wild type valines is underlined in FIG. 1A. Other nonsynonymous SNPs that have been identified in TSPYL include A74P (rs3749895) and P62S (rs3828743).

Complete genotyping of all 42 DNA samples in the SIDDT syndrome pedigree revealed that all four affected individuals were homozygous for the change, all parents of affected individuals were heterozygous, and no unaffected siblings were homozygous for the change. Fifty-eight Old Order Amish controls were genotyped for the insertion (n=116). Most of these samples were from Lancaster County Amish individuals; however, eight controls were available for study from the Juniata and Mifflin County Old Order Amish. None of the Lancaster County Old Order Amish carried the variant, but four heterozygotes were detected from the Mifflin and Juniata County Old Order Amish, suggesting that the 457_458insG variant has an especially high carrier frequency in this genetic isolate.

Individuals who may be carriers of a disease causing mutation may decide to undergo genetic screening to determine if the mutation is present. A couple who is planning a family may both choose to be tested. Reproductive decisions may be made based on the outcome of the test. For example, if the prospective mother and father each are carriers they may decide not to conceive or they may choose to use either an egg or a sperm donor. They may choose in vitro fertilization and have one or more embryos tested for genotype at the disease locus prior to implantation. Embryos that are not affected with the disease can be selected for implantation. In another aspect a fetus may be tested and the parents can choose to seek counseling to make informed decisions.

Parents who are carriers or suspect that they may be carriers may elect to have a child tested for the mutation soon after birth. The disease has been very difficult to diagnose and children were frequently subjected to numerous, costly tests and treatments in an effort to diagnose. Many of those tests can be avoided and replaced with a simple genetic test to determine if the child is homozygous for the mutation. In addition, accurate diagnosis will facilitate improved treatment regimens that are directed to the disease. Early and accurate diagnosis will allow caregivers to direct treatments to the phenotypes that are associated with the disease, for example, irregular breathing and heartbeat. In addition, once a child is diagnosed properly, treatments that are currently available for they known symptoms, for example, anti-seizure drugs and drug treatments for bradycardia, may be used to treat SIDDT.

The invention relates to isolated nucleic acid molecules comprising all or a fragment of a variant allele of TSPYL (e.g., wherein reference or wild type TSPYL is exemplified by SEQ ID NOs: 1 and 3). In one embodiment preferred fragments are at least 10, 12 or 15 contiguous nucleotides and comprise a polymorphic site, e.g. a fragment of SEQ ID NO: 3 or its complement which is at least 10, 12, or 15 nucleotides and further comprises an mutation, for example, an insertion at position 457_458 of the coding region. The invention further relates to isolated gene products, e.g., polypeptides or proteins, which are encoded by a nucleic acid molecule comprising all or at least a portion of the variant allele of TSPYL.

The invention also relates to isolated nucleic acid molecules which hybridize to the variant allele identified herein (or its complement) and not to the wild type allele under stringent hybridization conditions. The insertion detected is an insertion of a G nucleotide at a position that in the wild type already has two G nucleotides, therefore the insertion results in the presence of three G nucleotides in the mutant instead of two.

In one embodiment the mutation may be used to define a haplotype. The haplotype may be associated with SIDDT syndrome. Haplotype refers to a particular set of alleles at linked loci that are found together on a single chromosome and tend to be inherited together as a unit. The presence of a first mutation that is tightly linked to a second mutation can be determined by genotyping the second mutation. For example, if the 457_458insN mutation is linked to a second SNP with alleles A and B so that whenever the 457_458insN mutation is present, allele B is present at the second SNP, then the second mutation can be genotyped and the presence of the 457_458insN mutation can be inferred from the genotype of the second mutation.

The gene for TSPYL was first identified by a search of the EST database for sequences similar to Testis-Specific Protein, Y-encoded (TSPY) (Vogel et al., *Cytogenet Cell Genet* 81:265-270 (1998)). TSPYL (TSPY-Like) differs from TSPY in at least two important ways: (1) TSPY is found on the Y chromosome, whereas TSPYL is found on an autosomal chromosome and (2) TSPY is only found to be expressed in the testis, whereas TSPYL is broadly expressed in the testis, ovaries, prostates, brain, spleen kidney, lung, heart and liver. The biochemical and cellular function for TSPYL was previously unknown.

TSPYL contains a Nucleosome Assembly Protein (NAP) domain preceded by a region of low complexity. NAPs are a family of proteins that function as chaperones, shuttling histones from the cytosol to the nucleosome, and then shuttling unbound back to the cytosol. Consistent with this molecular function, studies of yeast NAP proteins show that NAPs are critical to nucleosome assembly, mitotic progression and chromatin formation. NAP domains may also function as transcription factors or gene regulators during embryogenesis. For example, during the development of Xenopus embryos, the NAP-containing protein NAP1L is broadly expressed at its highest level during development of hematopoietic tissue. When NAP1L is over expressed, genes involved in tissue development are up-regulated, specifically GATA-2, a gene essential for hematopoiesis (Steer, *Mech Dev.* 120(9):1045-57 (2003)). TSPYL may play a specific role in testicular development by altering regulation of other development genes and contributing to chromatin stability during cell division. Genotypic females are also affected by the mutation in TSPYL, suggesting that the gene, unlike TSPY, is expressed in other tissues. TSPYL may play a role in development by altering regulation of specific developmental genes and contributing to region-specific chromatin remodeling. TSPYL is highly expressed in fetal brain (GEO no. GSM14799). TSPYL has been shown to be negatively regulated in the hippocampus in a linear does-dependent fashion by corticosteroids (GEO no. GSM12543), sensitively negatively regulated by JNK2 (GEO no. GSM1514) and positively regulated by testosterone (GEO no. GSM6733). TSPYL may play a fundamental role in embryogenesis of the human nervous and reproductive systems. TSPYL expression and function in the developing brain may provide new insight into the genetic basis of apnea, dysphagia, cardiac arrests and sudden unexplained deaths in infancy. Present clinical evidence suggests that in SIDDT, sudden death may result from dysregulation of the autonomic brainstem systems that control cardiac and pulmonary protective reflexes. The lethal event may be profound vagally mediated laryngobronchospasm or asystole.

Methods are disclosed for detecting the presence of the 457_458insG allele. Samples that contain the mutant allele or mutant gene product may be identified by analysis of the TSPYL gene or gene product. Samples may be identified as being homozygous or heterozygous for the mutation. The genetic material to be assessed may be obtained from any nucleated cell from the individual. For assay of genomic DNA, virtually any biological sample (other than pure red blood cells) is suitable. For example, convenient tissue samples include whole blood, semen, saliva, tears, urine, fecal material, sweat, skin and hair. Buccal and blood samples are used in some embodiments. Samples may also be derived from archived tissue samples. In one aspect the sample may be obtained from chord blood. For assay of cDNA or mRNA, the tissue sample is preferably obtained from an organ in which the target nucleic acid is expressed.

In many embodiments genomic DNA may be obtained, for example, from amniotic fluid or from chorionic villus sampling (CVS). Amniotic fluid may be obtained, for example, by amniocentesis, where a needle is inserted through the mother's abdomen into the uterus (womb) and a small amount of fluid is withdrawn. CVS is performed by removing a small sample of the placenta from the uterus. It may be removed with a catheter or a needle. The sample may be obtained through the cervix or by insertion of a needle into the abdomen.

Many of the methods described herein require amplification of DNA from target samples. This can be accomplished by e.g., PCR. See generally PCR Technology: Principles and Applications for DNA Amplification (ed. H. A. Erlich, Freeman Press, N.Y., N.Y., 1992); PCR Protocols: A Guide to Methods and Applications (eds. Innis. et al., Academic Press, San Diego, Calif., 1990); Mattila et al., *Nucleic Acids Res.* 19, 4967 (1991); Eckert et al., PCR Methods and Applications 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4:560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The presence of the insertion at position 457 of TSPYL can be identified by a variety methods, such as Southern analysis of genomic DNA; Northern analysis of RNA; denaturing high pressure liquid chromatography (DHPLC); gene isolation and sequencing; hybridization of an allele-specific oligonucleotide with amplified gene products; single base extension (SBE) including SBE-FRET (see, U.S. Pat. No. 6,642,001); PCR-OLA, amplification refractory mutation system (ARMS), or analysis of the TSPYL protein. In a preferred embodiment, determination of the allelic form of TSPYL is carried out using allele-specific probes, or using chip-based oligonucleotide arrays. A sampling of suitable procedures is discussed below.

Allele-Specific Probes. The design and use of allele-specific probes for analyzing polymorphisms is described by e.g., Saiki et al., *Nature* 324, 163-166 (1986); EP 235,726, and WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Some probes are designed to hybridize to a segment of target DNA such that the polymorphic site aligns with a central position (e.g., in a 15-mer at the 7 position; in a 16-mer, at either the 8 or 9 position, in a 25-mer at the 13 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence. In some embodiments multiple probe pairs may be used for each polymorphism. The probe pairs may differ in the position of the polymorphic allele. See, for example, U.S. patent application Ser. No. 10/681,773.

The polymorphisms can also be identified by hybridization to nucleic acid arrays, some examples of which are described in WO 95/11995. WO 95/11995 also describes subarrays that are optimized for detection of a variant form of a pre-characterized polymorphism. Such a subarray contains probes designed to be complementary to a second reference sequence, which is an allelic variant of the first reference sequence. The second group of probes is designed by the same principles, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

Allele-Specific Primers. An allele-specific primer hybridizes to a site on target DNA overlapping a polymorphism and only primes amplification of an allelic form to which the primer exhibits perfect complementarity. See Gibbs, *Nucleic Acid Res.* 17, 2427-2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

ARMS (amplification refractory mutation system) is a PCR based technique in which an oligonucleotide primer that is complementary to either a normal allele or mutant allele is used to amplify a DNA sample. In one variation of this method, a pair of primers is used in which one primer is complementary to a known mutant sequence. If the DNA sample is amplified, the presence of the mutant sequence is confirmed. Lack of amplification indicates that the mutant sequence is not present. In a different variation, the primers are complementary to wild type sequences. Amplification of the DNA sample indicates that the DNA has the wild type sequence complementary to the primers. If no amplification occurs, the DNA likely contains a mutation at the sequence where hybridization should have occurred. A description of ARMS can be found in Current Protocols in Human Genetics, Chapter 9.8, John Wiley & Sons, ed by Dracopoli et al. (1995).

Direct-Sequencing. The direct analysis of the sequence of polymorphisms of the present invention can be accomplished using either the dideoxy chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

Denaturing Gradient Gel Electrophoresis. Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology, Principles and Applications for DNA Amplification, (W.H. Freeman and Co, New York, 1992), Chapter 7.

Single-Strand Conformation Polymorphism Analysis. Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

Single-Base Extension. Another method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (PNAS 94:10756-61 (1997), incorporated herein by reference) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

Immunological Assays. An immunological assay, such as an Enzyme Linked Immunoassay (ELISA), can be used as a diagnostic tool to determine whether or not an individual carries a mutation in TSPYL. One of skill in the art is familiar with the procedure for performing an ELISA. Briefly, antibodies are generated against native or mutant TSPYL. This can be accomplished by administering a native or mutant protein, or a peptide derived from a wild type or mutant protein, to an animal, such as a rabbit. The anti-TSPYL antibodies are purified and screened to determine specificity. In one representative example of an immunoassay, wells of a microtiter plate are coated with the specific anti-TSPYL antibodies. An aliquot of a sample from a patient to be analyzed for TSPYL protein is added in serial dilution to each antibody coated well. The sample is then contacted with labeled anti-TSPYL antibodies. For example, labeled anti-TSPYL antibodies, such as biotinylated anti-TSPYL antibodies, can be added to the microtiter plate as secondary antibodies. Detection of the label is correlated with the specific TSPYL antigen assayed. Other examples of suitable secondary antibody labels include radioactive isotopes, enzymes, fluorophores or chromophores. The presence of bound labeled (biotinylated) antibody is determined by the interaction of the biotin with avidin coupled to peroxidase. The activity of the bound peroxidase is easily determined by known methods.

Antibodies that bind to the wild type but not the mutant, the mutant but not the wild type or the mutant and the wild type may be generated. For example, an antibody that binds to the mutant but not the wild type may be generated by administering to the animal a peptide that is in the mutant but not the wild type. A wild type specific antibody may be raised to a peptide that is in the wild type but not the mutant and an antibody that binds to both mutant and wild type may be raised to a peptide that is present in both the mutant and wild type proteins. The antigenic agent may also be administered in a transfected cell. Antibodies may be polyclonal or monoclonal.

Polyclonal antibodies are made by immunizing an animal with a selected antigen. Repeated immunizations of the same antigen at intervals of several weeks, stimulates specific B cells to produce large amounts of antibodies to the antigen in the blood. Because many different B cells are stimulated by the antigen, the blood will contain a variety of antibodies to the antigen, each binding the antigen in a slightly different way. The immune-sera can be used in its crude form where high levels of specific antibodies are present, or the specific antibodies can be isolated from sera components by affinity purification.

To produce monoclonal antibodies the same immunization protocol may be used and all antibody forming cells may be removed. These are fused with immortal cells to become hybridomas, which are screened for antibody production. The hybridomas that produce antibodies are given clone names, which are uniquely assigned to permit identification. The antibody producing hybridomas are cloned and then the antibodies are isolated for cultivation by tissue culture. Unlike polyclonal antibodies these are homogeneous antibodies with defined specificity. The tissue culture supernatant can also be used in its crude form, or it can be further purified by affinity purification.

Production of TSPYL protein. The nucleic acid sequence encoding wild type or mutant TSPYL can be used to produce TSPYL in cells transformed with the sequence. For example, cells can be transformed by known techniques with an expression vector containing the TSPYL sequence operably linked to a functional promoter. Expression of TSPYL in transformed cells is useful in vitro to produce large amounts of the protein. Examples of suitable host cells include bacterial or yeast cells, for example. Additionally, mammalian cells, such as Chinese hamster ovary (CHO) cells can be used.

Due to degeneracy of the genetic code, most amino acids are encoded by more than one codon. Therefore, applicants recognize, and include within the scope of the invention, variations of the sequence shown in SEQ ID NOs: 3 and 4. For example, codons in a DNA sequence encoding TSPYL can be modified to reflect the optimal codon frequencies observed in a specific host. Rare codons having a frequency of less than about 20% in known sequences of the desired host are preferably replaced with higher frequency codon.

Transgenic Animals. The nucleic acid sequences encoding TSPYL, both wild type and mutant, provided in this application are useful for the development of transgenic animals expressing TSPYL. Such transgenic animals may be used, for example, to screen compounds for treating SIDDT syndrome. Useful variations of a transgenic animal are "knock out" or "knock in" animals. In a "knock out" animal, a known gene sequence, such as the sequence encoding TSPYL, is deleted from the animal's genome. Experiments can be performed on the animal, for example a mouse, to determine what effect the absence of the gene has on the animal. In a "knock in" experiment, the wild type gene is deleted and a mutant version or a gene from another organism is inserted, for example, a mutant or wild type human TSPYL gene. Experiments can be performed on the animal to determine the effects of this transition. A TSPYL homologue has been found in mouse.

Kits. The invention is also directed towards a kit for detecting mutation in the TSPYL gene. In one aspect a diagnostic kit may include a nucleic acid sequence encoding wild type TSPYL and at least one nucleic acid sequence encoding mutant TSPYL. In another aspect a kit includes at least one anti-TSPYL antibody which binds to mutant TSPYL and optionally an anti-TSPYL antibody which binds to wild type TSPYL. The antibody to the mutant may or may not bind to the wild type and the antibody to the wild type may or may not bind to the mutant. In another aspect a kit containing at least one pair of amplification primers capable of amplifying a at least part of the TSPYL DNA or RNA is disclosed. The kit may contain one or more allele specific primers that bind to the wild type and not to the mutant allele to be detected or one or more allele specific primers that bind to the mutant allele to be detected but not to the wild type.

In one aspect the kit contains one or more primer pairs for detection of a TSPYL mutation associated with disease, using an oligonucleotide ligation assay (OLA). An example of a pair of primers for OLA may include a first primer that binds to the region that is just 3' of the mutation and contains at the 3' end of the first primer the complement of the mutation, and a second primer that binds to the region that is immediately 5' of the mutation. If the mutation is present the primers when hybridized will be juxtaposed and can be ligated together, and the presence of the ligated product can be detected. If the mutation is not present the primers may still bind to the wild type form but there will be a mismatch at the 3' end of the first primer and ligation will be blocked. OLA is described in greater detail in U.S. Pat. No. 5,521,065.

In another aspect the kit may include one or more primers for single base extension detection (SBE). SBE primers may include a 5' tag sequence for detection and a 3' locus specific region that hybridizes to the target immediately 3' of the mutation. The SBE primer can be extended by one or more bases, including a base that is complementary to the mutation. The presence of the mutation can be detected by analyzing the extended SBE primer. In some embodiments the extended SBE primer is detected by detection of the tag sequence. Methods of mutation detection using SBE and an array of tag probes has been described in Fan et al., Gen. Res. 10(6):853-60 (2000).

In another aspect the kit comprises one or more molecular inversion probes (MIPs) as described in Hardenbol et al., Nat Biotechnol. 21(6):673f-678 (2003). MIPs based genotyping uses MIPs to produce inverted sequences, which undergo a unimolecular rearrangement and are then amplified by PCR using common primers and analyzed using universal sequence tag DNA microarrays. The MIP is a single probe that has a region that binds upstream of the polymorphism and a region that binds downstream of the polymorphism. The probe is gap filled with a base that is complementary to the polymorphism and ligated to form a circle. Circularized MIPs are amplified using universal priming sequences in the probe, more than 1,000 different MIPs can be amplified in parallel in a reaction. The probe also contains a tag sequence. The amplified tag sequence is labeled and detected to determine the presence of the mutation.

In another aspect the mutation can be detected by allele specific extension with sequence-coded identity tags as described in U.S. Pat. No. 6,287,778. Briefly, the region containing the mutation can be amplified, for example, by PCR using a pair of primers that are specific for the locus. One or more allele specific primers that terminate at the 3' end with a base that is complementary to the polymorphic allele are hybridized to the amplification product and extended by one or more bases, incorporating a label. The allele specific primers also have a 5' tag sequence that is unique for each allele specific primer. The extended primers are hybridized to a solid support, for example, a bead, with a probe complementary to the tag sequence. Hybridization is detected by detecting the presence of label.

Other methods for detection of a mutation include, amplification of all or part of the TSPYL DNA in the sample using a set of primers to produce amplified nucleic acids and sequencing the amplified nucleic acids; amplifying part of said TSPYL DNA in the sample using a primer specific for the mutation and detecting the presence of an amplified product, molecularly cloning all or part of the TSPYL DNA in the sample to produce a cloned nucleic acid and sequencing the cloned nucleic acid; amplifying the TSPYL DNA to produce amplified nucleic acids, hybridizing the amplified nucleic acids to a DNA probe specific for the mutation and detecting the presence of a hybridization product, forming single-stranded DNA from a gene fragment of said TSPYL DNA from the sample and single-stranded DNA from a corresponding fragment of a wild type gene, electrophoresing the single-stranded DNAs on a non-denaturing polyacrylamide gel and comparing the mobility of the single-stranded DNAs on the gel to determine if the single-stranded DNA from the sample is shifted relative to wild type and sequencing the single-stranded DNA having a shift in mobility; forming a heteroduplex consisting of a first strand of nucleic acid selected from the group consisting of a genomic DNA fragment isolated from said sample, an RNA fragment isolated from said sample and a cDNA fragment made from mRNA from the sample and a second strand of a nucleic acid consisting of a corresponding human wild type gene fragment, analyzing for the presence of a mismatch in the heteroduplex, and sequencing the first strand of nucleic acid having a mismatch; forming single-stranded DNA from said TSPYL DNA of said human sample and from a corresponding fragment of an allele specific for said mutation, electrophoresing said single-stranded DNAs on a non-denaturing polyacrylamide gel and comparing the mobility of said single-stranded DNAs on said gel to determine if said single-stranded DNA from said sample is shifted relative to said allele, wherein no shift in electrophoretic mobility of the single-stranded DNA relative to the allele indicates the presence of said mutation in said sample; and forming a heteroduplex consisting of a first strand of nucleic acid selected from the group consisting of a genomic DNA fragment of the TSPYL DNA isolated from the sample, an RNA fragment isolated from the sample and a cDNA fragment made from mRNA from the sample and a second strand of a nucleic acid consisting of a corresponding gene allele fragment specific for the mutation and analyzing for the presence of a mismatch in the heteroduplex, wherein no mismatch indicates the presence of the mutation.

In another aspect of the invention methods of treating SIDDT syndrome and methods of genetic therapy for the disease are also contemplated. The 457_458insG mutation results in a protein that does not perform the function of the wild type protein. Treatments may be developed to supplement the affected individual with functional protein. This may be done in utero or immediately after birth.

In another aspect of the invention methods for identification of individuals at risk for Sudden Infant Death syndrome (SIDS, OMIM #272120) are disclosed. The demonstrated association of the 457_458insG mutation with SIDDT and the similarity of the disease with SIDS make the TSPYL gene a candidate for a gene in which mutations that may be associated with one or more forms of SIDS may be identified. Other mutations in TSPYL and the surrounding region are candidates for SIDS associated mutations. To identify possible SIDS related mutations in TSPYL, the gene and surrounding regions may be sequenced in a collection of samples obtained from individuals who have died from SIDS. Such collections are available and could be sequenced to identify mutations in TSPYL that are present in individuals whose death was attributed to SIDS. Samples from SIDS victims may be sequenced in the TSPYL and TSPYL4 regions to identify novel mutations associated with the disease. Once mutations are identified larger sample populations can be genotyped at those SNPs.

The present invention may be better understood with reference to the following examples. These examples are intended to be representative of specific embodiments of the invention, and are not intended as limiting the scope of the invention.

EXAMPLES

Example 1

Mapping SIDDT

All DNA samples used in mapping and sequencing studies of SIDDT syndrome were acquired from patients and their families at the Clinic for Special Children, Strasburg, Pa. Over the past two generations, nine families from the Old Order Amish community of Mifflin and Juniata counties have lost twenty-one infants to a disorder locally known as Swarey syndrome. Samples were collected from affected individuals, their parents, and siblings. In addition, samples from other sibships were collected based on medical records and family interviews which indicated that affected children had been born into these families.

Comprehensive genealogies for all affected individuals were prepared from private and published family records.

SNP Genotyping was done using the GeneChip® Mapping 10K Mapping Array and Assay Kit (Affymetrix, Inc., Santa Clara, Calif.). This protocol is slightly modified from Kennedy et al. *Nat. Biotechnol.* 21:1233-1237 (2003). DNA from whole blood was isolated by using the PUREGENE DNA Isolation Kit (Gentra Systems). 250 ng of double-stranded genomic DNA was digested with XbaI (New England Biolabs (NEB)) for 2 hr at 37° C. followed by heating for 20 min at 70° C. Digested DNA was then incubated in a reaction containing with 0.25 µM Xba adapter (Affymetrix) and DNA ligase (NEB) in standard ligation buffer (NEB) for 2 hr at 16° C. followed by heat inactivation for 20 min at 70° C. Ligated products were amplified in quadruplicate using a concentration of 0.5 µM of the supplied generic primer XbaI (Affymetrix) in PCR Buffer II (Applied Biosystems) with 2.5 mM $MgCl_2$, 250 µM each DNTP and 10 units of AmpliTaq Gold polymerase (Applied Biosystems) under the following PCR conditions: 95° C. for 5 min, followed by 35 cycles of 95° C. for 20 sec, 59° C. for 15 sec, 72° C. for extension at 72° C. for 7 min. Fragments in the 250 to 1,000 base pair size range are preferentially amplified under these conditions. PCR products were purified with the QIAaquick PCR purification kit (Qiagen) according to the manufacturer's recommendations with the exception of the elution procedure. DNA from each of 4 PCR replicate samples was bound to separate columns and washed. The eluant collected from column 1 was used to elute the remaining 3 columns in series. The final purified product is the combination of 4 purified PCR product samples. 18-20 µg of purified PCR products were fragmented with 0.24 units of the supplied GeneChip® Fragmentation Reagent (Affymetrix) for 30 min at 37° C. followed by a heat inactivation for 15 min at 95° C. Samples were then labeled with 15-20 units of terminal deoxytransferase (Affymetrix) and 0.143 mM of supplied GeneChip® DNA Labeling Reagent in TdT buffer (Affymetrix) for 2 hr at 37° C. followed by heat inactivation for 15 min at 95° C. After end-labeling, the fragments were hybridized to a GeneChip® Human Mapping 10K Array for 16-18 hr at 48° C. while rotating at 60 rpm. Microarrays were then washed using the Fluidics Station 450 (Affymetrix) in 0.6×SSPE (sodium chloride, sodium phosphate, EDTA), followed by a three-step staining protocol. We incubated the arrays first with 10 ug/mL streptavidin (Pierce), washed with 6×SSPE and incubated with 5 ug/mL biotinylated anti-streptavidin (Vector Lab) and 10 ug/mL streptavidin-phycoerythrin conjugate (Molecular Probes), and finally washed with 6×SSPE as per manufacturers recommended times. Microarrays were scanned using the GeneChip® Scanner 3000 according to the manufacturer protocol (Affymetrix). Data acquisition was performed using the GeneChip® GCOS software. Initial data analysis was done using the GeneChip® DNA Analysis Software and then exported to SNPSpring or VARIA (Silicon Genetics) for analysis.

Linkage mapping: SNP positions came from dbSNP build 115 and NCBI build 33 or 34v2 of the human genome. VARIA searches for genomic regions that are identical by descent between all affected individuals and assumes no mutation heterogeneity within affected individuals. Genotypes came from the Affymetrix 10K SNP Mapping Arrays. An algorithm for autozygosity mapping appropriate for recessive diseases with sibships from a genetically isolated population using dense SNP maps was used for analysis. The method assumes no mutation heterogeneity within affected individuals. The software searches for genomic regions which are identical-by-descent between all affected individuals. Details on the generation of "location scores" can be found on the Silicon Genetics website. Two-point LOD scores were calculated for each of the 11,555 SNPs genotyped using an approach similar to Broman and Weber *Am. J. Hum. Genet.* 65:1493-1500, (1999), generalizing the algorithm to include multiple affected individuals and their parents. In addition, several assumptions were made for the analysis including a genotype error rate of 1%, Hardy-Weinberg equilibrium, and linkage equilibrium for alleles at adjacent marker loci for the first pass analysis. Using these assumptions, LOD scores were calculated for each SNP individually, representing the ratio of the likelihood of observing the measured SNPs given autozygosity at that locus in the affected individuals relative to the likelihood of observing the individual SNPs given no autozygosity at that locus. One hyndred seventy Old Order Amish Control chromosomes (including 6 untransmitted chromosomes from the SIDDT syndrome parents and 38 from the three mapping validation sibships) were used as controls to estimate SNP allele frequencies. Genomic regions of contiguous markers that exhibited the highest sum of individual LOD scores were identified and ranked. Cumulative two-point LOD scores for a block of SNPs were considered the LOD score for the region. The calculated LOD scores were used to ascertain genomic regions worthy of further investigation. Analyses were repeated using haplotype blocks defined in a similar manner to Daly et al. *Nat Genet* 29:229-232 (2001). The haplotype blocks were then treated as individual genetic markers. The results were very similar to the two-point LOD score approach used for microsatellite marker mapping where they are assumed to be in linkage equilibrium with respect to one another.

The three regions of the genome having the highest location scores were 6q22.1-q22.31 with a location score of 8.11, 9q32-q33.1 with location score of 6.18 and 11q22.2 with location score of 5.94. The four affected individuals are homozygous for 13 adjacent SNPs at the 6q22 locus. The region is bounded by SNPs rs1388219 and rs1321370. The gene content of the interval contained 18 characterized and 9 hypothetical genes. The characterized genes in the interval are: MARCKS, FLJ34503, HDAC2, HS3ST5, FRK, NT5C2L1, COL10A1, TSPYL4, RPS5P1, TSPYL, SART2, C6orf188, C6orf78, RWDD1, C6orf113, KPNA5, GPRC6A, and RFXDC1. For additional information see, Puffenberger et al. *PNAS* 101:11689-11694 (2004).

Example 2

Sequencing Candidate Genes

Mutation analysis was performed for two candidate genes in the linked region on chromosome 6q22.1c-q22.2d: TSPYL and TSPYL4 (Genbank #AL050331 contains both genes). The exon of each target gene was amplified using specific oligonucleotide primers and 30-50 ng of genomic DNA from affected and unaffected family members. The TSPYL gene lacks introns and contains a coding region of 1,314 bases (GenBank accession no. AL050331). The mRNA is about 3200 bases in length (GenBank XM_371844) and the mature TSPYL protein is 437 amino acids. Primer sequences for TSPYL PCR amplification were

```
(forward)
5'-AGATCTCCAGTCCTGACGACAC-3'    (SEQ ID NO: 6)
and (reverse)
5'-AGGAAACAGGGTGCAGAAAAGT-3'.   (SEQ ID NO: 7)
```

Primer sequences for PCR amplification of TSPYL4 were

```
AAAACTCCCCTTCCAGACTGAC          (SEQ ID NO: 8)
and

CACAATGCAGAAAAGCATGAAG.         (SEQ ID NO: 9)
```

PCR products were purified using QiaQuick columns (Qiagen) as per manufacturer's instructions, and then sequenced using the BigDye Terminator cycle sequencing protocol (Applied Biosystems). TSPYL sequencing primers were

```
TSPYL1036-F:
GGCCGAGTGGTGTCTCTTTCTA;         (SEQ ID NO: 10)

TSPYL618-F:
GGAGGATAGATTGGAGGAGGAG;         (SEQ ID NO: 11)

TSPYL237-F:
TACTCCCCAGATCCGAGTTGTT.         (SEQ ID NO: 12)
```

TSPYL4 sequencing primers were:

```
TSPYL4C277-F:
ACACAGGTGATGGCGAACACAG;         (SEQ ID NO: 13)

TSPYL4C776-F:
CCATCGATCAAGAGTTGTCAAA;         (SEQ ID NO: 14)

TSPYL4C1165-F:
CAGGCTCATATCCACAGAAACC;         (SEQ ID NO: 15)

TSPYL4C889-R:
TAATGAAACTTCTGCGCTGCAT.         (SEQ ID NO: 16)
```

Extension products were subsequently size-fractionated on an ABI 310 Genetic Analyzer. Sequences were compared to normal mRNA and genomic sequence for each gene from GenBank AL050331 in order to identify sequence variants. Population-based control samples were sequenced in an identical fashion.

Example 3

Subcellular Localization of Mutant and Wild Type TSPYL Protein

Full-length and truncated TSPYL cDNAs were amplified using gene-specific primers for the full-length: forward, CACCATGAGCGGCCTGGATGGGGTCAAGAGG (SEQ ID NO: 17); reverse, TAGCTCGAGACCAGACTGGAAC-CCAAAGGGCCTGGGGATC (SEQ ID NO: 18); and the truncated: forward, CACCATGAGCGGCCTG-GATGGGGTCAAGAGG (SEQ ID NO: 19); reverse, TAGCTC GAGTGGCGGCTGCTCCTCTACCTCC (SEQ ID NO: 20) versions from genomic DNA using AmpliTaq Gold® (Applied Biosystems) or the Expand High Fidelity PCR System (Roche, Indianapolis). Cycling conditions were an initial denaturation step of 94° C. for 2 min followed by 30 cycles of 94° C. for 15 sec, 68° C. for 1 min, and 72° C. final extension step at 72° C. for 10 min with AmpliTaq or 94° C. for 2 min followed by 9 cycles of (94° C. for 15 sec, 68° C. for 1 min, and 68° C. for 105 sec) followed by 94° C. for 25 sec and then 24 cycles of (68° C. for 1 min, 72° C. for 3 min), with a final extension step at 72° C. for 12 min. for Expand. PCR products were cloned directionally into entry vector pENTR-D-TOPO Gateway vector (Invitrogen) and then into the Gateway destination vector pcDNA-DEST47 (Invitrogen) containing a C-terminal GFP tag. All clones were sequence verified. $10^5$ HeLa$_{F2}$ cells ($10^5$) were grown in DMEM supplemented with 10% FBS (Gibco) and then switched to opti-MEM medium (Invitrogen) and transfected with 2-4 µg of the TSPYL (full-length and truncated) GFP constructs using Lipofectin Reagent (Invitrogen) according to the manufacturer's recommendations. 24 hours after transfection, subconfluent HeLa$_{F2}$ cells were washed three times with phosphate-buffered saline (PBS) and these transiently transformed cells were fixed in 2% formaldehyde and permeabilized in 0.1% Triton X-100 to perforate all cellular membrane. Nuclear localization was confirmed using 4',6-diamidino-2-phenylindole dihydrochloride stain from Molecular Probes. Images were captured with FITC and UV filter sets and a 100× oil immersion objective in conjunction with a Leica TCS-NT confocal microscope. TSPYL localizes to the nucleus with a punctuate staining pattern, whereas the truncated form shows diffuse cytoplasmic staining.

CONCLUSION

The above description is illustrative and not restrictive. Many variations of the invention will become apparent to those of skill in the art upon review of this disclosure. The scope of the invention should, therefore, be determined not with reference to the above description, but instead be determined with reference to the appended claims along with their full scope of equivalents.

We claim:

1. A method of detecting a mutant TSPYL gene carrying a 457_458 insertion comprising:

hybridizing an isolated nucleic acid sequence to a nucleic acid sample wherein said isolated nucleic acid sequence comprises at least 16 contiguous nucleotides of SEQ ID NO. 4 or its complement, spans positions 457 and 458 of the coding region of the TSPYL gene and comprises the 457_458ins mutation, under conditions where the nucleic acid sequence hybridizes with a nucleic acid derived from a TSPYL gene having the 457_458ins mutation to generate a hybridization complex but not to a nucleic acid derived from a wild type TSPYL gene;

and detecting the presence or absence of said hybridization complex, wherein the presence of said hybridization complex indicates the presence of a TSPLY gene carrying a 457_458 insertion.

2. The method of claim 1 wherein said isolated nucleic acid sequence is labeled.

3. The method of claim 1 wherein the nucleic acids in the nucleic acid sample are labeled.

4. A method to identify a subject that carries a mutant TSPYL gene associated with SIDDT syndrome comprising:

determining that a TSPYL 457_458insG gene or gene product is present in a biological sample from the subject, and identifying said subject as carrying a mutant TSPYL gene associated with SIDDT syndrome if the TSPYL 457_458insG gene or gene product is present.

5. The method of claim 4 wherein the step of determining comprises performing an in vitro nucleic acid assay.

6. The method of claim 5 wherein the in vitro nucleic acid assay comprises PCR amplification of all or part of the TSPYL gene or a nucleic acid derived from a TSPYL gene.

7. The method of claim 6 wherein the PCR amplification is allele specific.

8. The method of claim 5 wherein said nucleic acid assay comprises a hybridization assay with allele specific probes.

9. The method of claim 8 wherein the hybridization assay comprises:

hybridizing a nucleic acid probe to said nucleic acid sample, said nucleic acid probe spanning the 457_458insG mutation in the TSPYL gene; and detecting hybridization of said probe wherein hybridization is indicative of the presence of the 457_458insG mutation and the presence of a TSPYL 457_458insG gene.

* * * * *

UNITED STATES PATENT AND TRADEMARK OFFICE
CERTIFICATE OF CORRECTION

PATENT NO. : 7,632,640 B2
APPLICATION NO. : 11/007924
DATED : December 15, 2009
INVENTOR(S) : Puffenberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 553 days.

Signed and Sealed this

Second Day of November, 2010

David J. Kappos
*Director of the United States Patent and Trademark Office*

SEQUENCE LISTING

```
<160> NUMBER OF SEQ ID NOS: 20

<210> SEQ ID NO 1
<211> LENGTH: 438
<212> TYPE: PRT
<213> ORGANISM: Homo sapiens

<400> SEQUENCE: 1

Met Ser Gly Leu Asp Gly Val Lys Arg Thr Thr Pro Leu Gln Thr His
 1               5                  10                  15

Ser Ile Ile Ile Ser Asp Gln Val Pro Ser Asp Gln Asp Ala His Gln
            20                  25                  30

Tyr Leu Arg Leu Arg Asp Gln Ser Glu Ala Thr Gln Val Met Ala Glu
        35                  40                  45

Pro Gly Glu Gly Gly Ser Glu Thr Val Ala Leu Pro Pro Pro Pro
    50                  55                  60

Ser Glu Gly Gly Val Pro Gln Asp Ala Ala Gly Arg Gly Gly Thr
65                  70                  75                  80

Pro Gln Ile Arg Val Val Gly Gly Arg Gly His Val Ala Ile Lys Ala
                85                  90                  95

Gly Gln Glu Glu Gly Gln Pro Pro Ala Glu Gly Leu Ala Ala Ala Ser
            100                 105                 110

Val Val Met Ala Ala Asp Arg Ser Leu Lys Lys Gly Val Gln Gly Gly
        115                 120                 125

Glu Lys Ala Leu Glu Ile Cys Gly Ala Gln Arg Ser Ala Ser Glu Leu
    130                 135                 140

Thr Ala Gly Ala Glu Ala Glu Ala Glu Val Lys Thr Gly Lys Cys
145                 150                 155                 160
```

-continued

```
Ala Thr Val Ser Ala Val Ala Glu Arg Glu Ser Ala Glu Val Val
            165                 170                 175

Val Lys Glu Gly Leu Ala Glu Lys Glu Val Met Glu Gln Met Glu
        180                 185                 190

Val Glu Glu Gln Pro Pro Glu Gly Glu Ile Glu Val Ala Glu Glu
            195                 200                 205

Asp Arg Leu Glu Glu Glu Ala Arg Glu Glu Gly Pro Trp Pro Leu
    210                 215                 220

His Glu Ala Leu Arg Met Asp Pro Leu Glu Ala Ile Gln Leu Glu Leu
225                 230                 235                 240

Asp Thr Val Asn Ala Gln Ala Asp Arg Ala Phe Gln Gln Leu Glu His
                245                 250                 255

Lys Phe Gly Arg Met Arg Arg His Tyr Leu Glu Arg Arg Asn Tyr Ile
            260                 265                 270

Ile Gln Asn Ile Pro Gly Phe Trp Met Thr Ala Phe Arg Asn His Pro
        275                 280                 285

Gln Leu Ser Ala Met Ile Arg Gly Gln Asp Ala Glu Met Leu Arg Tyr
    290                 295                 300

Ile Thr Asn Leu Glu Val Lys Glu Leu Arg His Pro Arg Thr Gly Cys
305                 310                 315                 320

Lys Phe Lys Phe Phe Phe Arg Arg Asn Pro Tyr Phe Arg Asn Lys Leu
                325                 330                 335

Ile Val Lys Glu Tyr Glu Val Arg Ser Ser Gly Arg Val Val Ser Leu
            340                 345                 350

Ser Thr Pro Ile Ile Trp Arg Arg Gly His Glu Pro Gln Ser Phe Ile
        355                 360                 365

Arg Arg Asn Gln Asp Leu Ile Cys Ser Phe Phe Thr Trp Phe Ser Asp
    370                 375                 380

His Ser Leu Pro Glu Ser Asp Lys Ile Ala Glu Ile Ile Lys Glu Asp
385                 390                 395                 400

Leu Trp Pro Asn Pro Leu Gln Tyr Tyr Leu Leu Arg Glu Gly Val Arg
                405                 410                 415

Arg Ala Arg Arg Pro Leu Arg Glu Pro Val Glu Ile Pro Arg Pro
            420                 425                 430

Phe Gly Phe Gln Ser Gly
            435

<210> SEQ ID NO 2
<211> LENGTH: 168
<212> TYPE: PRT
<213> ORGANISM: Homo sapiens

<400> SEQUENCE: 2

Met Ser Gly Leu Asp Gly Val Lys Arg Thr Thr Pro Leu Gln Thr His
1               5                   10                  15

Ser Ile Ile Ile Ser Asp Gln Val Pro Ser Asp Gln Asp Ala His Gln
                20                  25                  30

Tyr Leu Arg Leu Arg Asp Gln Ser Glu Ala Thr Gln Val Met Ala Glu
            35                  40                  45

Pro Gly Glu Gly Gly Ser Glu Thr Val Ala Leu Pro Pro Pro Pro
        50                  55                  60

Ser Glu Glu Gly Gly Val Pro Gln Asp Ala Ala Gly Arg Gly Thr
65                  70                  75                  80

Pro Gln Ile Arg Val Val Gly Gly Arg Gly His Val Ala Ile Lys Ala
                85                  90                  95
```

Gly Gln Glu Glu Gly Gln Pro Pro Ala Glu Gly Leu Ala Ala Ala Ser
            100                 105                 110

Val Val Met Ala Ala Asp Arg Ser Leu Lys Lys Gly Val Gln Gly Gly
        115                 120                 125

Glu Lys Ala Leu Glu Ile Cys Gly Ala Gln Arg Ser Ala Ser Glu Leu
    130                 135                 140

Thr Ala Gly Ala Glu Ala Glu Ala Gly Gly Glu Asp Arg Lys Val
145                 150                 155                 160

Arg His Arg Leu Ser Ser Arg Gly
                165

<210> SEQ ID NO 3
<211> LENGTH: 3259
<212> TYPE: DNA
<213> ORGANISM: Homo sapiens

<400> SEQUENCE: 3

| | | |
|---|---|---|
| agtgagactg tagggtgggc ggtgcgagcg gcggttagct cccagttcgg cctctgagga | 60 |
| aaacgggcgt tcgcctgcgg ttggtccgac tgttagcaac atgagcggcc tggatggggt | 120 |
| caagaggacc actcccctcc aaacccacag catcattatt tctgaccaag tcccgagcga | 180 |
| ccaggacgca caccagtacc tgaggctccg cgaccaaagc gaggcgacac aggtgatggc | 240 |
| ggagccgggt gagggaggct cggagaccgt cgcgctcccg cctccaccgc cttcagagga | 300 |
| gggggggcgta ccccaggatg ccgcgggccg tgcggtact ccccagatcc gagttgttgg | 360 |
| gggtcgcggt catgtggcga tcaaagccgg gcaggaagag ggccagcctc ccgccgaagg | 420 |
| cctggcagcc gcttctgtgg tgatggcagc cgaccgcagc ctgaaaaagg gcgttcaggg | 480 |
| tggagagaag gccctagaaa tctgtggcgc ccagagatcc gcgtctgagc tgacggcggg | 540 |
| ggcggaggct gaggcggagg aggtgaagac aggaaagtgc gccaccgtct cagcagccgt | 600 |
| ggctgagagg gagagcgctg aggtggtggt gaaggaaggc ctggcggaga aggaggtaat | 660 |
| ggaggagcag atggaggtag aggagcagcc gccagaaggt gaagaaatag aagtggcgga | 720 |
| ggaggataga ttggaggagg aggcgaggga ggaagaaggg ccctggcctt tgcatgaggc | 780 |
| tctccgcatg gaccctctgg aggccatcca gctggaactg acactgtgaa atgctcaggc | 840 |
| cgacagggcc ttccaacagc tggagcacaa gtttgggcgg atgcgtcgac actacctgga | 900 |
| gcggaggaac tacatcattc agaatatccc gggcttctgg atgactgctt ttcgaaacca | 960 |
| ccccagttg tccgccatga ttaggggcca agatgcagag atgttaaggt acataaccaa | 1020 |
| tttagaggtg aaggaactca gacaccctag aaccggttgc aagttcaagt tcttctttag | 1080 |
| aagaaacccc tacttcagaa acaagctgat tgtcaaggaa tatgaggtaa gatcctccgg | 1140 |
| ccgagtggtg tctctttcta ctccaattat atggcgcagg gggcatgaac cccagtcctt | 1200 |
| cattcgcaga aaccaagacc tcatctgcag cttcttcact tggttttcag accacagcct | 1260 |
| tccagagtcc gacaaaattg ctgagattat taagaggat ctgtggccaa atccactgca | 1320 |
| atactacctg ttgcgtgaag gagtccgtag agcccgacgt cgcccgctaa gggagcctgt | 1380 |
| agagatcccc aggccctttg ggttccagtc tggttaacat ttgcccttgg gaatactcct | 1440 |
| gcacaaggtc tcctaccacc ttctgctgga cctgtgcttg gcatcagca atgagtatgc | 1500 |
| cttctattgt gctttgtttt tgctgacttt tatgcaccct gtttcctttg gatattcagt | 1560 |
| tctctcaacc tcaagattga gacggtggtg ggtatgcttc tccacttcca tatgaccttc | 1620 |
| atgctgttct ggaatatcac atgctacgag gtcatccttc acactacttg taagccaagc | 1680 |

```
aaatgatact gtagattgta ctgcctttat ctgcactgct tggaccctgt ttattcccag    1740
ggcctctgaa ctggttgctg tcacttggat ttctagcttt gggagcctgt tccacctact    1800
cagctctgca ttgagcagta tgggcacatg ccctgtggac agttactgga cgttaatgaa    1860
ctcagaggag aaaagcagtg agccacttgt tctgtgtgat ttatggtact tcattgctct    1920
tccttcacct ctagtcactt tctattgcta cctgccctac attggctcct gccaaggtcc    1980
ctctctctcc ctgttttcct ttttttttt ttttttttt tgagacggag gacggagtct     2040
tgctctgtcg cccaggttgg agtgcagtgg cgcgatctcg gctcactgca acctccacct    2100
cccgggttca gcgattctc ctgcctcagc ctcccgagta gctgggacta caggcgcgcg     2160
ccgccacgcc cggctaattt ttatatttt agtagagacg gggtttcacc atgctggcca     2220
ggctggtctc gaaccccgac ctcgtgatcc gccctcctta gcctcccaat cctctcttaa    2280
aaaagtgata gctcagaaac atttgtaaaa gcaaggtttt tatttcattt tggctctgtc    2340
attttcagag gcaaagaagt tggcctgtaa aatagagtgc tagagctctt acgcccctcc    2400
ccttcttccc aacttcctac ttcctagccc ttttatcaac tcctagaata gttaaagaga    2460
gacacatcta gatgggatga aggtgccct aagcaggaga aactgaacaa aaggctagag     2520
gcatgggcca ggtaaaaatt gggcctgag tgaagactgt gctgtcgtta agagctttcg     2580
aggaaggagt acttactccc caatgatgat gaatggaaaa atacttttca gggagaattg    2640 aagggggttaa agtgttaaat atgttgccta gacaagggtt ctttaaagaa agacagcgca    2700
actttgaatg ctttcttact tgttttgtga cctaatttat gtggaagatt gttatttcat    2760
taggatttag taaaatttt ttttctgatt ctaaacttat tgtgaaaatt gagctgtaca     2820
gatattcttt tgatttcaat tgggaacatt tggaagaaca acagtcttac ttgcctgtac    2880
aatatagaga catatgaata gtcataacag ttttcaactt gttcttgttt ctgttaaact    2940
atattcctag aaacatagtt tgaacaactt ggtctttgtt aggcttgtca aattgccttc    3000
atggaaaaat aatctacaaa agtatggttt aattgattgt cttacatgat aattttccct    3060
ggtaacaact tagtaagtga tatatctttt ttcctaaatt gcttaaatac tgtgaaattg    3120
ctctgacaaa ttggaagtgt accattggca tatttgtctt cctttttatg catgatggta    3180
aaataaaagc atgttgttct gctaaaaaaa aaaaaaaaa aaaaaaaaa aaaaaaaaa      3240 aacaaaaaaa aaaaaaaaa                                                3259

<210> SEQ ID NO 4
<211> LENGTH: 3260
<212> TYPE: DNA
<213> ORGANISM: Homo sapiens

<400> SEQUENCE: 4
agtgagactg tagggtgggc ggtgcgagcg gcggttagct cccagttcgg cctctgagga      60
aaacgggcgt tcgcctgcgg ttggtccgac tgttagcaac atgagcggcc tggatggggt    120
caagaggacc actcccctcc aaacccacag catcattatt tctgaccaag tcccgagcga    180
ccaggacgca caccagtacc tgaggctccg cgaccaaagc gaggcgacac aggtgatggc    240
ggagccgggt gagggaggct cggagaccgt cgcgctcccg cctccaccgc cttcaggaga    300 gggggcgta cccccaggatg ccgcggggcg tggcggtact ccccagatcc gagttgttgg    360
gggtcgcggt catgtggcga tcaaagccgg gcaggaagag ggccagcctc ccgccgaagg    420
cctggcagcc gcttctgtgg tgatggcagc cgaccgcagc ctgaaaaagg gcgttcaggg    480
```

-continued

```
tggagagaag gccctagaaa tctgtggcgc ccagagatcc gcgtctgagc tgacggcggg    540
ggcggaggct gaggcgggag gaggtgaaga caggaaagtg cgccaccgtc tcagcagccg    600
tggctgagag ggagagcgct gaggtggtgg tgaaggaagg cctggcggag aaggaggtaa    660
tggaggagca gatggaggta gaggagcagc cgccagaagg tgaagaaata gaagtggcgg    720
aggaggatag attggaggag gaggcgaggg aggaagaagg gccctggcct ttgcatgagg    780
ctctccgcat ggaccctctg gaggccatcc agctggaact ggacactgtg aatgctcagg    840
ccgacagggc cttccaacag ctggagcaca gtttgggcg gatgcgtcga cactacctgg    900
agcggaggaa ctacatcatt cagaatatcc cgggcttctg gatgactgct tttcgaaacc    960
acccccagtt gtccgccatg attaggggcc aagatgcaga gatgttaagg tacataacca   1020
atttagaggt gaaggaactc agacaccta gaaccggttg caagttcaag ttcttctta   1080 gaagaaaccc ctacttcaga aacaagctga ttgtcaagga atatgaggta agatcctccg   1140
gccgagtggt gtctctttct actccaatta tatggcgcag ggggcatgaa ccccagtcct   1200
tcattcgcag aaaccaagac ctcatctgca gcttcttcac ttggttttca gaccacagcc   1260
ttccagagtc cgacaaaatt gctgagatta ttaaagagga tctgtggcca aatccactgc   1320
aatactacct gttgcgtgaa ggagtccgta gagcccgacg tcgcccgcta agggagcctg   1380
tagagatccc caggcccttt gggttccagt ctggttaaca tttgcccttg gaatactcc   1440 tgcacaaggt ctcctaccac cttctgctgg acctgtgctt gggcatcagc aatgagtatg   1500
ccttctattg tgctttgttt ttgctgactt ttatgcaccc tgtttccttt ggatattcag   1560
ttctctcaac ctcaagattg agacggtggt gggtatgctt ctccacttcc atatgacctt   1620
catgctgttc tggaatatca catgctacga ggtcatcctt cacactactt gtaagccaag   1680
caaatgatac tgtagattgt actgccttta tctgcactgc ttggaccctg tttattccca   1740
gggcctctga actggttgct gtcacttgga tttctagctt tgggagcctg ttccacctac   1800
tcagctctgc attgagcagt atgggcacat gccctgtgga cagttactgg acgttaatga   1860
actcagagga gaaaagcagt gagccacttg tctgtgtga tttatggtac ttcattgctc   1920
ttccttcacc tctagtcact ttctattgct acctgcccta cattggctcc tgccaaggtc   1980
cctctctctc cctgttttcc ttttttttt tttttttttt ttgagacgga ggacggagtc   2040
ttgctctgtc gcccaggttg gagtgcagtg gcgcgatctc ggctcactgc aacctccacc   2100
tcccgggttc aagcgattct cctgcctcag cctcccgagt agctgggact acaggcgcgc   2160
gccgccacgc ccggctaatt tttatatttt tagtagagac ggggtttcac catgctggcc   2220
aggctggtct cgaaccccga cctcgtgatc cgccctcctt agcctcccaa tcctctctta   2280
aaaaagtgat agctcagaaa catttgtaaa agcaaggttt ttatttcatt ttggctctgt   2340
cattttcaga ggcaaagaag ttggcctgta aaatagagtg ctagagctct tacgcccctc   2400
cccttcttcc caacttccta cttcctagcc cttttatcaa ctcctagaat agttaaagag   2460
agacacatct agatgggatg aaaggtgccc taagcaggag aaactgaaca aaaggctaga   2520
ggcatgggcc aggtaaaaat tgggcctaga gtgaagactg tgctgtcgtt aagagctttc   2580
gaggaaggag tacttactcc ccaatgatga tgaatggaaa aatactttc agggagaatt   2640 gaaggggtta aagtgttaaa tatgttgcct agacaagggt tctttaaaga aagacagcgc   2700
aactttgaat gctttcttac ttgttttgtg acctaattta tgtggaagat tgttatttca   2760
ttaggattta gtaaaatttt ttttctgat tctaaactta ttgtgaaaat tgagctgtac   2820
agatattctt ttgatttcaa ttgggaacat ttggaagaac aacagtctta cttgcctgta   2880
```

```
caatatagag acatatgaat agtcataaca gttttcaact tgttcttgtt tctgttaaac    2940
tatattccta gaaacatagt ttgaacaact tggtctttgt taggcttgtc aaattgcctt    3000
catggaaaaa taatctacaa aagtatggtt taattgattg tcttacatga taattttccc    3060
tggtaacaac ttagtaagtg atatatcttt tttcctaaat tgcttaaata ctgtgaaatt    3120
gctctgacaa attggaagtg taccattggc atatttgtct tccttttat gcatgatggt     3180 aaaataaaag catgttgttc tgctaaaaaa aaaaaaaaaa aaaaaaaaaa aaaaaaaaaa    3240
aaacaaaaaa aaaaaaaaaa                                                3260

<210> SEQ ID NO 5
<211> LENGTH: 71
<212> TYPE: DNA
<213> ORGANISM: Homo sapiens

<400> SEQUENCE: 5
gcgtctgagc tgacggcggg ggcggaggct gaggcgggag gaggtgaaga caggaaagtg    60
cgccaccgtc t                                                         71

<210> SEQ ID NO 6
<211> LENGTH: 22
<212> TYPE: DNA
<213> ORGANISM: Homo sapiens

<400> SEQUENCE: 6
agatctccag tcctgacgac ac                                             22

<210> SEQ ID NO 7
<211> LENGTH: 22
<212> TYPE: DNA
<213> ORGANISM: Homo sapiens

<400> SEQUENCE: 7
aggaaacagg gtgcagaaaa gt                                             22

<210> SEQ ID NO 8
<211> LENGTH: 22
<212> TYPE: DNA
<213> ORGANISM: Homo sapiens

<400> SEQUENCE: 8
aaaactcccc ttccagactg ac                                             22

<210> SEQ ID NO 9
<211> LENGTH: 22
<212> TYPE: DNA
<213> ORGANISM: Homo sapiens

<400> SEQUENCE: 9
cacaatgcag aaaagcatga ag                                             22

<210> SEQ ID NO 10
<211> LENGTH: 22
<212> TYPE: DNA
<213> ORGANISM: Homo sapiens

<400> SEQUENCE: 10
ggccgagtgg tgtctctttc ta                                             22

<210> SEQ ID NO 11
```

```
<211> LENGTH: 22
<212> TYPE: DNA
<213> ORGANISM: Homo sapiens

<400> SEQUENCE: 11
ggaggataga ttggaggagg ag                                              22

<210> SEQ ID NO 12
<211> LENGTH: 22
<212> TYPE: DNA
<213> ORGANISM: Homo sapiens

<400> SEQUENCE: 12
tactccccag atccgagttg tt                                              22

<210> SEQ ID NO 13
<211> LENGTH: 22
<212> TYPE: DNA
<213> ORGANISM: Homo sapiens

<400> SEQUENCE: 13
acacaggtga tggcgaacac ag                                              22

<210> SEQ ID NO 14
<211> LENGTH: 22
<212> TYPE: DNA
<213> ORGANISM: Homo sapiens

<400> SEQUENCE: 14
ccatcgatca agagttgtca aa                                              22

<210> SEQ ID NO 15
<211> LENGTH: 22
<212> TYPE: DNA
<213> ORGANISM: Homo sapiens

<400> SEQUENCE: 15
caggctcata tccacagaaa cc                                              22

<210> SEQ ID NO 16
<211> LENGTH: 22
<212> TYPE: DNA
<213> ORGANISM: Homo sapiens

<400> SEQUENCE: 16
taatgaaact tctgcgctgc at                                              22

<210> SEQ ID NO 17
<211> LENGTH: 31
<212> TYPE: DNA
<213> ORGANISM: Homo sapiens

<400> SEQUENCE: 17
caccatgagc ggcctggatg gggtcaagag g                                    31

<210> SEQ ID NO 18
<211> LENGTH: 40
<212> TYPE: DNA
<213> ORGANISM: Homo sapiens

<400> SEQUENCE: 18
tagctcgaga ccagactgga acccaaaggg cctgggatc                            40
```

```
<210> SEQ ID NO 19
<211> LENGTH: 31
<212> TYPE: DNA
<213> ORGANISM: Homo sapiens

<400> SEQUENCE: 19
caccatgagc ggcctggatg gggtcaagag g                              31

<210> SEQ ID NO 20
<211> LENGTH: 31
<212> TYPE: DNA
<213> ORGANISM: Homo sapiens

<400> SEQUENCE: 20
tagctcgagt ggcggctgct cctctacctc c                              31
```